US00PP29608P3

(12) United States Plant Patent
Irvine

(10) Patent No.: US PP29,608 P3
(45) Date of Patent: Aug. 21, 2018

(54) ***PASSIFLORA* PLANT NAMED 'SNOW QUEEN'**

(50) Latin Name: *Passiflora caerulea*
Varietal Denomination: Snow Queen

(71) Applicant: Myles S. Irvine, Surbiton (GB)

(72) Inventor: Myles S. Irvine, Surbiton (GB)

( * ) Notice: Subject to any disclaimer, the term of this patent is extended or adjusted under 35 U.S.C. 154(b) by 29 days.

(21) Appl. No.: 15/330,633

(22) Filed: Oct. 20, 2016

(65) Prior Publication Data

US 2017/0202118 P1 Jul. 13, 2017

(30) Foreign Application Priority Data

Jan. 7, 2016 (QZ) ..... PBR 2016/0047

(51) Int. Cl.
*A01H 5/02* (2018.01)

(52) U.S. Cl.
USPC ..... Plt./226

(58) Field of Classification Search
USPC ..... Plt./226
See application file for complete search history.

*Primary Examiner* — Keith O. Robinson
(74) *Attorney, Agent, or Firm* — Barbara Campbell; James M. Weatherly; Cochran Freund & Young LLC

(57) ABSTRACT

A new variety of *Passiflora* named 'Snow Queen' that is characterized by large entirely white flowers consisting of white petals, white sepals and white corona filaments. The petals and sepals of 'Snow Queen' are thick and waxy. 'Snow Queen' is highly floriferous, hardy in USDA zone 8b, vigorous and bears strong dark green leathery foliage.

3 Drawing Sheets

Genus and species: *Passiflora caerulea.*
Variety denomination: 'Snow Queen'.

CROSS-REFERENCE TO RELATED APPLICATIONS

This application claims the benefit of priority under 35 U.S.C. § 119 to an application filed with the European Community Plant Variety Office, which was filed for the instant plant variety on Jan. 7, 2016, File Number 2016/0047. 'Snow Queen' has not been made publicly available or sold more than one year prior to the filing date of the present application.

BACKGROUND OF THE NEW PLANT

The present invention relates to a new and distinct variety of *Passiflora* commonly known as Passion Flower or Passion Vine that is grown for use as an ornamental plant for planting in gardens and in the landscape. Plants of *Passiflora* may also be trained for use as container grown plants. The new variety is known botanically as *Passiflora caerulea*, and will be referred to hereinafter by the cultivar name 'Snow Queen'.

'Snow Queen' resulted from a formal breeding program that was established by the inventor in 2002 in Surbiton, Surrey, United Kingdom. The inventor has made close study of the genus *Passiflora* and has bred several varieties with improved garden performance, including improved hardiness and vigor combined with larger flower size, longer-lasting flowers and unique color combinations of petals, sepals and corona.

'Snow Queen' is the result of the inventor's deliberate pollination of *Passiflora* 'White Wedding' (unpatented), as the female parent with the male parent, an un-named and un-released seedling of the species *Passiflora caerulea* which the inventor had raised and retained from previous breeding. The inventor chose the female parent for its presumed polyploid characteristics and chose the male parent for its extra hardiness since it alone had survived outside through a hard winter.

From the seedlings arising from the pollination as described, the inventor selected 'Snow Queen' in 2011 for the purity of its large white flowers which exhibit long-lasting qualities and for the vigor and hardiness of the plants themselves. Based on his experience and expertise in the genus and its cultivars, the inventor considers that 'Snow Queen' is very likely to be a triploid variety.

The first asexual propagation of 'Snow Queen' was accomplished by the inventor in 2011 in the inventor's garden in Surbiton, Surrey, United Kingdom. The method of propagation was rooting of soft and semi-hard stem cuttings. The inventor has observed through repeated propagations of 'Snow Queen' that 'Snow Queen' is stable and reproduces true to type in successive generations of asexual propagation via rooting of soft and semi-hard stem cuttings.

SUMMARY

The following represent the distinguishing characteristics of the new *Passiflora* cultivar 'Snow Queen'. In combination, these characteristics set 'Snow Queen' apart from all other existing varieties of *Passiflora* known to the inventor.

1. 'Snow Queen' exhibits large white flowers consisting of white petals, sepals and corona filaments.
2. The petals and sepals of 'Snow Queen' are thick and waxy.
3. 'Snow Queen' is highly floriferous, producing many buds and flowers simultaneously on an established plant.
4. 'Snow Queen' is readily propagated using softwood cuttings.

5. 'Snow Queen' is hardier than many varieties of the species: 'Snow Queen' has survived in temperatures of −8° C.
6. The leaves of 'Snow Queen' are dark green in color, strong and leathery in texture, and glossy or semi-glossy on their upper surfaces.

DESCRIPTION OF THE PHOTOGRAPHS

The accompanying color drawings illustrate the overall appearance of the new *Passiflora* variety 'Snow Queen' showing the colors as true as it is reasonably possible to obtain in colored reproductions of this type. Colors in the drawings may differ from the color values cited in the detailed botanical description, which accurately describes the actual colors of the new variety, 'Snow Queen'. All photographs were made from plants growing outdoors in Surbiton, Surrey, United Kingdom.

DESCRIPTION OF THE NEW VARIETY

Figure 1:
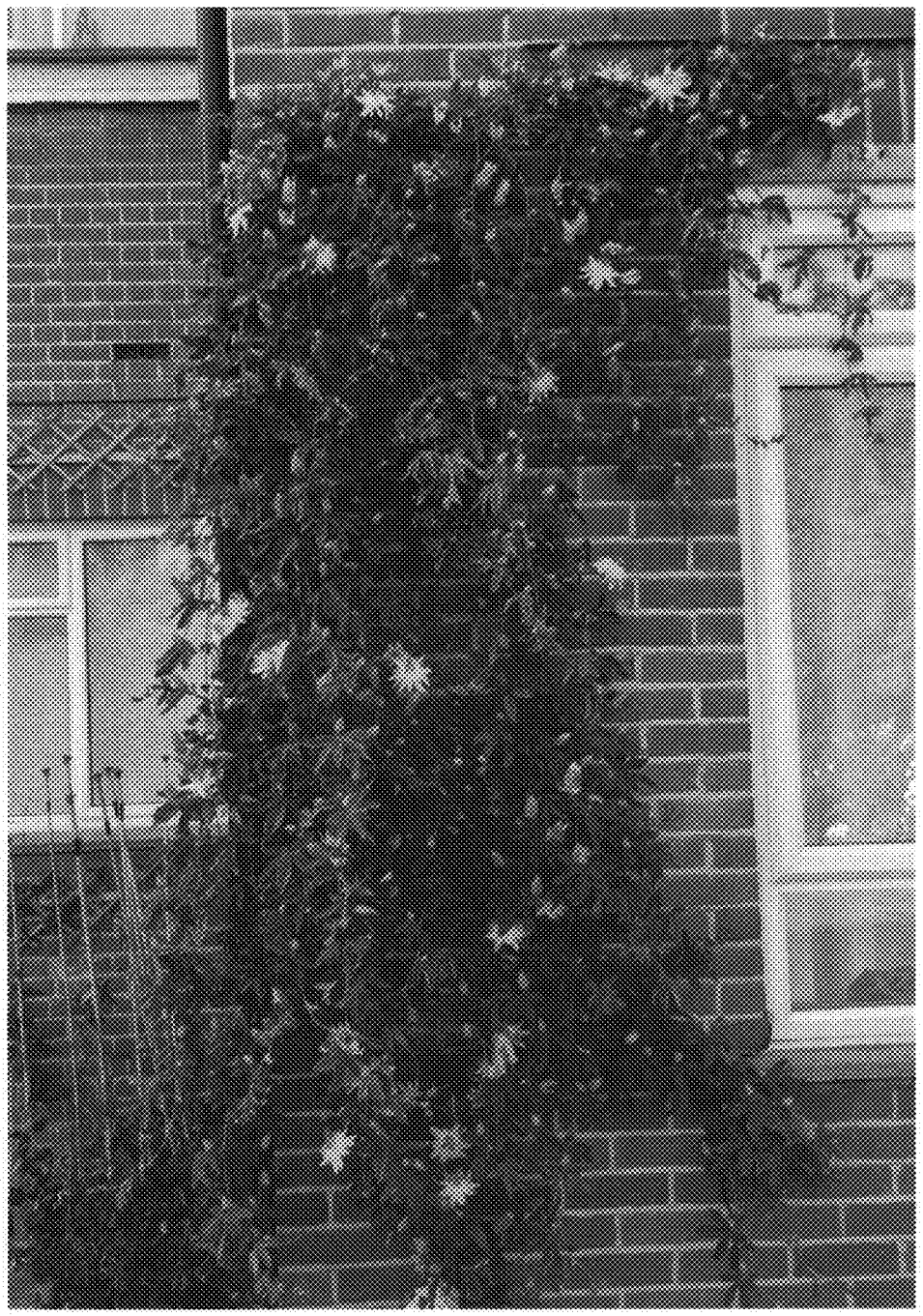
FIG. 1 depicts a whole vining plant of 'Snow Queen' growing against a wall. The illustrated plant is fifteen-months-old.
Figure 2:
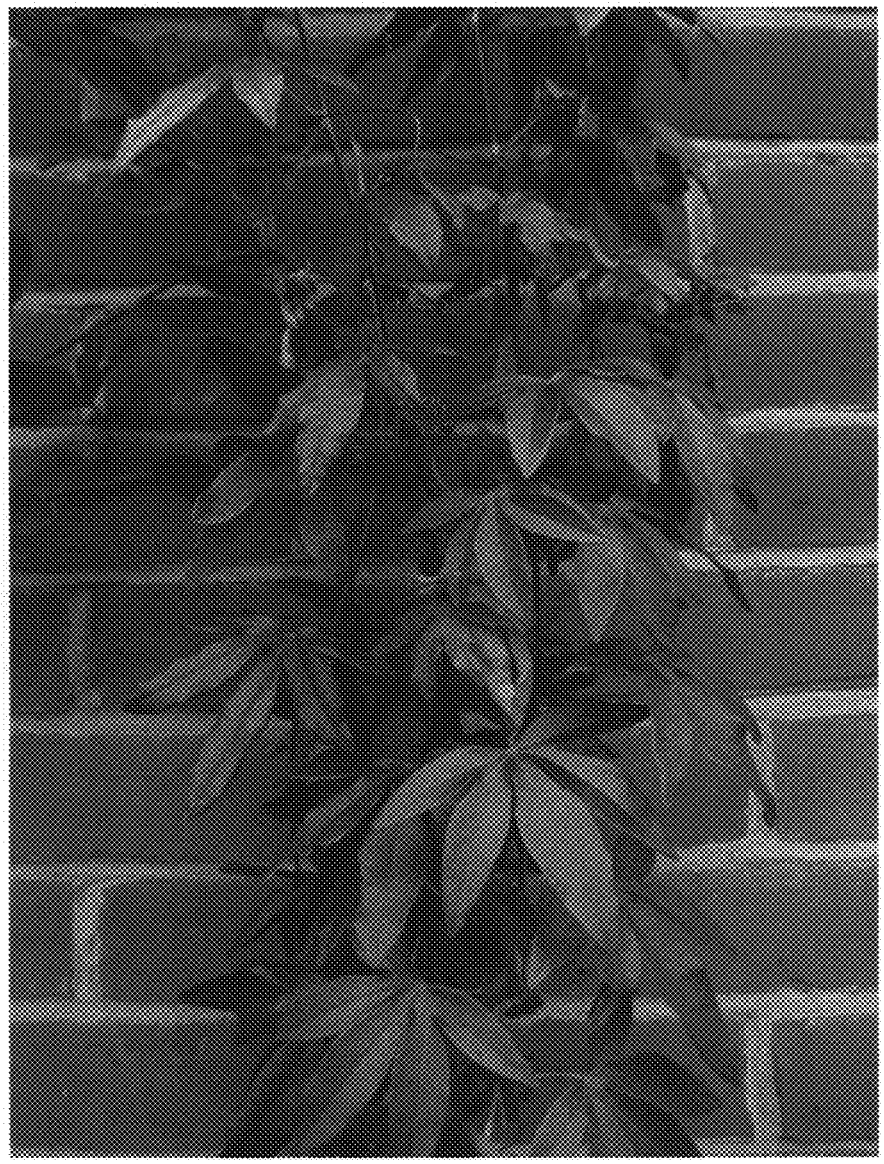
FIG. 2 depicts a close-up view of the dark green, strong, leathery foliage of 'Snow Queen' of the plant of FIG. 1.
Figure 3:
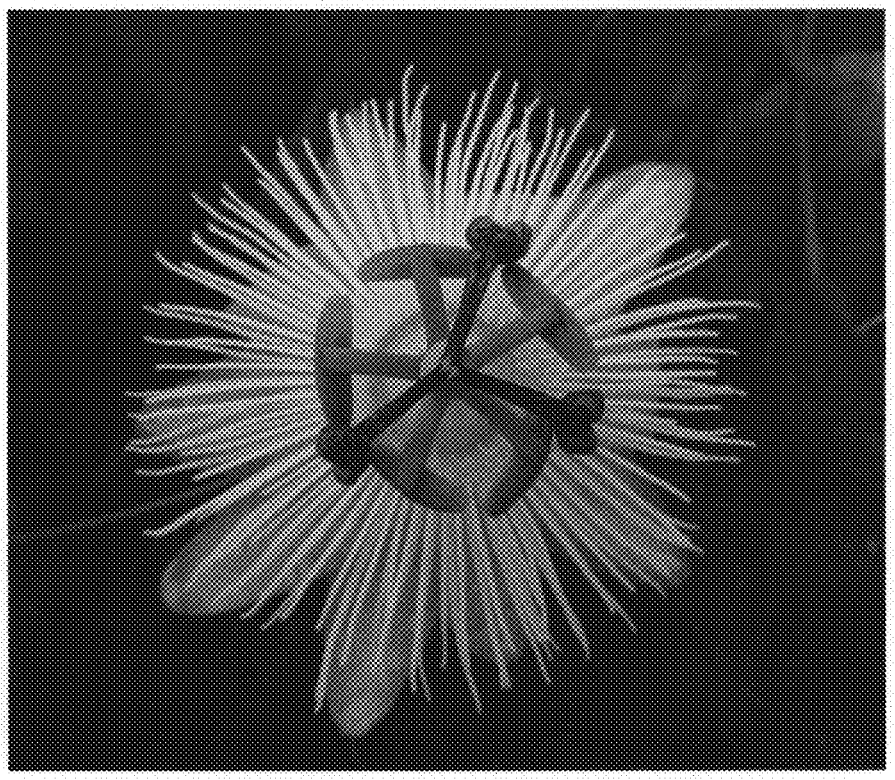
FIG. 3 depicts a close-up view from above of a flower of 'Snow Queen' of the plant of FIG. 1.
Figure 4:
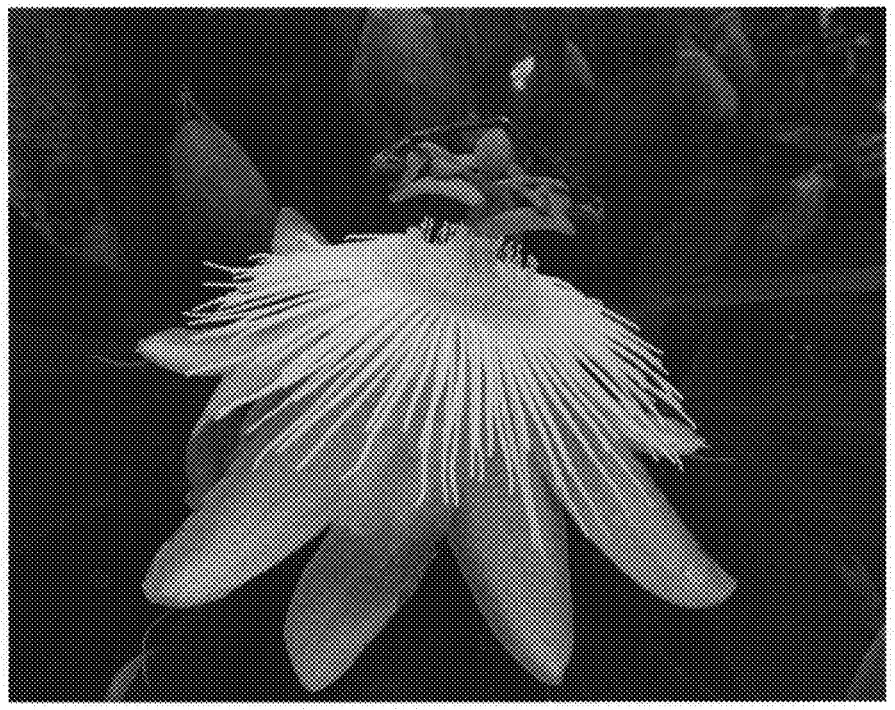
FIG. 4 depicts a close-up side view of a flower of 'Snow Queen' when reflexing of the plant of FIG. 1. This photograph illustrates (from top to bottom) the styles and stigma, the ovary, the stamens and lightly suspended anthers, the operculum of fine upright filaments, the corona of lateral filaments and finally the alternating sepals and petals.

The following is a detailed description of the *Passiflora* cultivar named 'Snow Queen'. Data was collected in Surbiton, United Kingdom from a fifteen-month-old plant growing outdoors. Color determinations are in accordance with The 2007 Royal Horticultural Society Colour Chart except where general color terms of ordinary dictionary significance are used. The growing requirements are similar to the species.

Botanical classification:

*Genus and species.*—*Passiflora caerulea.*

*Denomination.*—'Snow Queen'.

*Common name.*—Passion flower, Passion vine.

Parentage:

*Female parent.*—*Passiflora* 'White Wedding' (unpatented).

*Male parent.*—A seedling of *Passiflora caerulea* raised by the inventor (un-named and unpatented).

Plant:

*Use.*—Vining garden ornamental for planting against walls or on trellises, or trained for use in planted containers.

*Type.*—Semi-deciduous vine.

*Vigor.*—Vigorous, grows rapidly from spring until fall.

*Habit.*—Vining.

*Height or length* (*at maturity*).—8 meters.

*Width* (*at maturity*).—4 meters.

*Hardiness.*—USDA Zone 8b; plants have been observed to survive above −8° C.

*Propagation.*—Softwood cuttings.

*Time to initiate rooting.*—3 weeks at air or soil temperature of 22° C.; a young plant will be well-rooted in 6 weeks.

*Root system.*—Slightly fleshy, strong, freely branching; root diameter up to 3.0 mm, color 155A.

*Soil requirement.*—Moist, well-drained soils, avoiding very wet soils.

*Sunlight preference.*—Full-sun is preferred.

*Crop time.*—12 to 15 weeks (from transplanting a rooted cutting) are needed to produce a budded and flowering plant in a 1-liter container.

*Disease and pests.*—'Snow Queen' is susceptible to viruses which are common to the genus, notably *Passiflora mosaic* virus (genus *Potyvirus*, species unknown). 'Snow Queen' is similarly susceptible to common plant pests, notably thrips (*Thripidae*) and spider mites (*Tetranychus*).

Stem:

*Shape.*—Cylindrical, stiff, wiry.

*Dimensions.*—3.0 m in length and 4.0 mm in diameter.

*Surface texture.*—Glabrous.

*Color.*—Initially 144A (juvenile growth and apical growth); where exposed to sun, longitudinal striations of 187A; at maturity, entire surface is colored 187A and 187B.

*Internode length.*—6.0 cm to 12.0 cm between nodes.

*Branching habit.*—Stimulated by pruning; lateral branches may emerge at each node.

Foliage:

*Type.*—Semi-evergreen.

*Leaf strength.*—Strong.

*Surface texture.*—Leathery.

*Leaf surface appearance.*—Glossy or semi-glossy (adaxial surface); matte (abaxial surface).

*Arrangement.*—Alternate.

*Type.*—Compound, predominantly 5-lobed, occasionally 3-lobed.

*Attachment.*—Petiolate.

*Petioles.*—Length: 4.0 cm to 5.0 cm. Diameter: 2.0 mm to 3.0 mm. Color: 146C, aging through 175D to 187A. Petiole glands: 4 to 9 ovoid glands, 2.0 mm to 3.0 mm in length, arranged singly or in pairs towards upper section of petiole; nectar has not been observed.

*Stipules.*—Arranged in irregular pairs at each node; 3.0 cm in length, 1.5 cm in width, color 136A.

*Tendrils.*—One per node, tightly spiraled, wiry, strong; unfurled length approximately 17.0 cm, diameter 2.0 mm to 3.0 mm; color ranges between 146C and 175D.

*Compound leaf.*—Dimensions (maximum): 15.0 cm in length and 22.0 cm in width. Lobes: Dimensions: Central (largest) lobe up to 15.0 cm in length; 4.0 cm in width; outer lobes (2 pairs or 1 pair) 12.0 cm in length; 2.5 cm to 3.0 cm in width. Apex: Acute. Base: Fused to adjacent lobes. Margin: Smooth, entire, undulating. Color (both surfaces): New growth 144A; mature foliage ranges between 137A and 136A and occasionally very dark N189A. Venation: Palmate; prominent fold along midrib; midrib appears lighter in color than adjacent lamina, occasionally turns maroon, 187A.

Inflorescence:

*General description.*—Strong flower held proud of foliage consisting of tube bearing five sepals, five petals and many threadlike membranes (together, the corona) above which are five prominent anthers, the ovary and three prominent stigmas and styles.

*Blooming season.*—Continually from spring through summer, including hot summers, and into fall; first buds have been observed in February in southern England.

*Quantity of flowers.*—At peak flowering, a fifteen-month-old plant of 'Snow Queen' bears approximately 150 buds and 30 open or opening flowers.

*Lastingness of flowers on the plant.*—2 to 3 days.

*Fragrance.*—Slightly sweet.

*Peduncle.*—Shape and aspect: Cylindrical; upright or at right angles to stem. Dimensions: 5.0 cm in length, 3 mm in diameter. Color: 143C.

*Bracts.*—3 in number, free, basally fused to peduncle, 1.8 cm in length.

*Buds.*—Shape is obconical; apex is rounded, sepal awns extending up to 5.0 mm; base is rounded; dimensions (immediately prior to opening), length is 7.0 cm and diameter 3.0 cm; color is 144B.

*Flower dimensions.*—11.0 cm 12.0 cm in diameter when petals and sepals fully opened; petals and sepals reflex with age.

*Sepals.*—5 in number, narrowly ovate, 4.0 cm to 5.0 cm in length, 1.5 cm in width; surface texture fleshy and waxy; color NN155C and translucent 154D towards apex (both surfaces); apex is rounded (except for awns); base is truncate; sepal awn (attached to apex) is recurving crescent-like and length up to 5.0 mm.

*Petals.*—5 in number, alternating with sepals, narrowly ovate, 4.0 cm to 5.0 cm in length, 1.5 cm in width; surface texture is fleshy; color NN155C (both surfaces); petal apex is rounded; base is truncate.

*Corona.*—Consists of two layers of rod-like filaments, 50 to 70 filaments per layer; filament length ranges between 7.5 cm and 8.0 cm; filaments in upper layer are slightly longer; filament diameter is 1.5 mm; filament color is pure white, whiter than NN155D, very occasional light violet-blue tints, 92C or lighter, have been observed towards filament tips under early and late season cooler conditions.

Reproductive organs:

*Operculum.*—Inner corona of upright rod-like filaments arranged in tight concentric rings; filament length ranges between 1.0 mm and 2.0 mm, diameter less than 1 mm; very numerous filaments, at least 100 in number per flower; color is pure white, whiter than NN155D.

*Androgynophore.*—Tubular, approximately 1.0 cm in diameter; 1.5 cm in height; color is 146D.

*Stamens.*—5 in number; filaments flattened, width 7.0 mm, length 30.0 mm to 35.0 mm, color is 146D with light speckling N187A towards anther attachment.

*Anthers.*—Prominent, elliptic, 45.0 mm in length, 15.0 mm in width, color is 146D; anther attachment is loosely minutely attached, anther hangs with adaxial (pollen-bearing); aspect is surface downwards.

*Pollen.*—Dark yellow 17A, sparse, concentrated around and below perimeter of anther.

*Ovary.*—Superior; shape ellipsoidal, 18.0 cm in diameter; surface, glossy; color, 157D.

*Styles.*—3 in number, strong, rigid, joined above ovary, length (including stigma) 5.0 cm.

*Color.*—146D with heavy mottling N187A.

*Stigma.*—Bifurcated; overall width 2 cm, depth 0.5 cm; color is 146D with mottling of N187A.

Fruit, seed: Produced very rarely: less than one fruit per 100 flowers; where observed, shape is ovoid; color is RHS 143D green ripening to RHS 17A yellow-orange; dimensions are 6.5 cm in length, 4.0 cm in diameter; seed (mostly observed immature) is 30 to 40 seeds in number, including many aborting; seed shape is ellipsoid; seed color is RHS 145B pale green; seed dimensions are approximately 6.0 mm in length, 2.0 mm in diameter; where seeds have matured, color RHS 200A dark brown, surface reticulated.

COMPARISON TO PARENTAL LINES AND COMMERCIAL VARIETY

'Snow Queen' may be distinguished from its parents as follows. In comparison with the female parent, 'White Wedding' (unpatented), 'Snow Queen' has survived in hard winters whereas 'White Wedding' has died. The foliage of 'Snow Queen' is vigorous with consistent thick dark green leaves, whereas the foliage of 'White Wedding' is variable in vigor and slightly lighter in color. Both 'White Wedding' and 'Snow Queen' bear white flowers.

In comparison with the male parent, a seedling of the species *P. caerulea*, 'Snow Queen' bears all-white flowers whereas the species bears predominantly blue flowers.

The varieties of *Passiflora* which the inventor considers most closely resemble 'Snow Queen' are *Passiflora* 'White Wedding', compared above, and *Passiflora* 'Constance Eliott' (unpatented). Whereas the white flowers of 'Constance Eliott' are 8 cm to 9 cm in diameter with 4 cm to 5 cm long corona filaments, the flowers of 'Snow Queen' are 11 cm to 12 cm in diameter with filaments between 7.5 and 8.0 cm in length. The flowers of 'Constance Eliott' usually open and close the same day whereas the flowers of 'Snow Queen' may open for two days or more. In addition, whereas the foliage of 'Constance Eliott' is typical of the species, the foliage of 'Snow Queen' is thick, strong and leathery in texture and with larger leaves.

I claim:

1. A new and distinct variety of *Passiflora* plant named 'Snow Queen' as illustrated and described herein.

* * * * *